United States Patent [19]

Muntwyler

[11] 4,336,270
[45] Jun. 22, 1982

[54] O-BENZYLPHENOLS

[75] Inventor: Rene Muntwyler, Hofstetten, Switzerland

[73] Assignee: Ciba-Geigy Corporation, Ardsley, N.Y.

[21] Appl. No.: 82,188

[22] Filed: Oct. 5, 1979

Related U.S. Application Data

[63] Continuation of Ser. No. 856,939, Dec. 2, 1977, abandoned, which is a continuation of Ser. No. 678,771, Apr. 20, 1976, abandoned, which is a continuation of Ser. No. 510,937, Oct. 1, 1974, abandoned.

[30] Foreign Application Priority Data

Oct. 29, 1973 [CH] Switzerland ............. 15200/73

[51] Int. Cl.³ ............... C07C 39/367; A01N 31/08
[52] U.S. Cl. .................... 424/347; 424/340; 424/341; 568/745; 568/649; 568/656; 252/8.9; 252/8.6; 252/106; 424/59; 424/70; 424/69; 424/65
[58] Field of Search ............ 568/745, 649; 424/347, 424/340

[56] References Cited

U.S. PATENT DOCUMENTS

| 1,880,566 | 10/1932 | Werler et al. | 568/745 |
| 2,872,489 | 2/1959 | Dietzler et al. | 568/745 |
| 3,277,164 | 10/1966 | Haack | 568/745 |
| 3,787,507 | 1/1974 | Debat | 568/745 |
| 3,830,852 | 8/1974 | Debat | 568/745 |
| 3,833,672 | 9/1974 | Debat | 568/745 |
| 3,855,317 | 10/1974 | Debat | 568/745 |
| 3,984,482 | 10/1976 | Debat | 568/745 |
| 4,031,248 | 6/1977 | Schellenbaum et al. | 424/347 |
| 4,057,648 | 11/1977 | Hool et al. | 424/347 |
| 4,111,844 | 9/1978 | Polony et al. | 424/347 |
| 4,124,520 | 11/1978 | Schwalley et al. | 424/347 |

FOREIGN PATENT DOCUMENTS

| 260914 | 5/1963 | Australia | 568/745 |
| 824058 | 7/1949 | Fed. Rep. of Germany | 568/745 |
| 1200M | 11/1960 | France | 568/745 |
| 1298927 | 11/1960 | France | 568/745 |
| 1345874 | 12/1962 | France | 568/745 |
| 75088 | 9/1968 | German Democratic Rep. | 568/745 |
| 417785 | 1/1933 | United Kingdom | 568/745 |
| 916506 | 1/1963 | United Kingdom | 568/745 |
| 935161 | 8/1963 | United Kingdom | 568/745 |
| 1300753 | 9/1973 | United Kingdom | 568/745 |

OTHER PUBLICATIONS

Bun Hoi et al., J. Org. Chem., Vol. 20, pp. 1129–1134 (1955).
Huston et al., J.A.C.S., Vol. 55, pp. 4639–4643 (1933).
McKay et al., J-Med. Chem. Vol. 6, pp. 816–817 (1963).
Klarmann et al., J.A.C.S. Vol. 54, pp. 3315–3328 (1932).

Primary Examiner—Natalie Trousof
Assistant Examiner—James H. Reamer
Attorney, Agent, or Firm—Edward McC. Roberts; John P. Spitals

[57] ABSTRACT

Novel o-benzylphenols as well as a process for their production, a method for combating harmful microorganisms and compositions comprising said o-benzylphenols are provided.

17 Claims, No Drawings

O-BENZYLPHENOLS

This is a continuation of application Ser. No. 856,939 filed on Dec. 2, 1977 now abandoned, which is a continuation application of Ser. No. 678,771, filed on Apr. 20, 1976, now abandoned which in turn is a continuation application of Ser. No. 510,937, filed on Oct. 1, 1974 now abandoned.

The present invention provides novel o-benzylphenols, a process for their manufacture, a method of using them for combating harmful microorganisms, and compositions containing these novel compounds.

Ortho-benzylphenols are known from British patents 916 506 and 935 161, German patent 824 058, DOS 2 211 266, and J.A.C.S. 54 3315 (1932). Surprisingly, the novel, specially substituted o-benzylphenols provided by the invention have a substantially better action against Gram-positive and Gram-negative bacteria and against fungi than the compounds of the prior art.

The novel o-benzylphenols have the formula

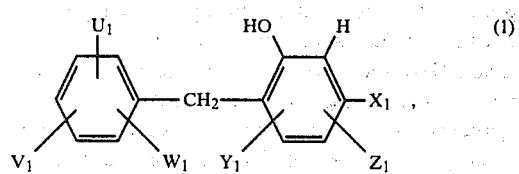

wherein $X_1$ represents halogen, $Y_1$ represents hydrogen, halogen, alkyl with 1 to 4 carbon atoms or alkoxy with 1 to 4 carbon atoms, $Z_1$ represents hydrogen or halogen, $U_1$ represents hydrogen, halogen or alkyl with 1 to 4 carbon atoms, $V_1$ represents hydrogen, halogen or alkyl with 1 to 4 carbon atoms, and $W_1$ represents hydrogen, alkyl with 1 to 4 carbon atoms, alkoxy with 1 to 4 carbon atoms or trifluoromethyl.

Within the scope of the formula (1), compounds with an increasingly interesting utility are those of the formulae

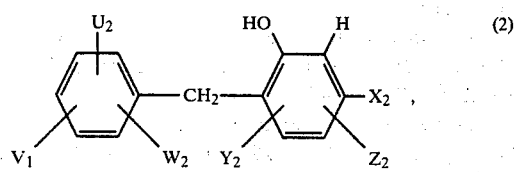

wherein $X_2$ represents chlorine or bromine, $Y_2$ represents hydrogen, bromine or methyl, $Z_2$ represents hydrogen, chlorine or bromine, $U_2$ represents hydrogen, fluorine chlorine, bromine or methyl, $V_2$ represents hydrogen, fluorine, chlorine, bromine or methyl, and $W_2$ represents hydrogen, methyl or trifluoromethyl;

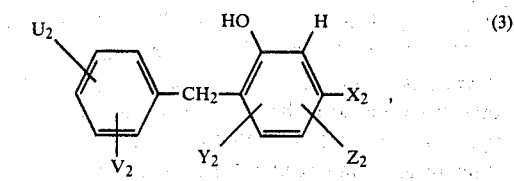

wherein $X_2$, $Y_2$, $Z_2$, $U_2$ and $V_2$ have the meanings previously assigned to them;

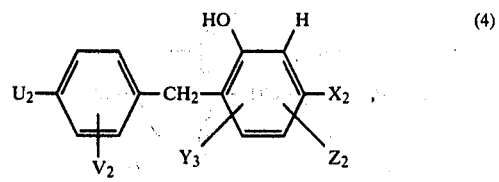

wherein $Y_3$ represents hydrogen, chlorine or bromine and $X_2$, $Z_2$, $U_2$ and $V_2$ have the meanings previously assigned to them;

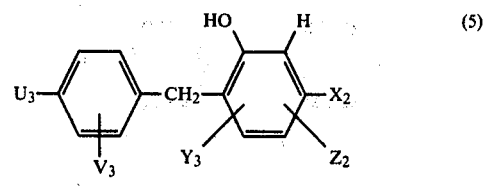

wherein $X_2$, $Z_2$ and $Y_3$ have the meanings previously assigned to them and one of the substituents $U_3$ and $V_3$ represents fluorine, chlorine or bromine and the other represents hydrogen, chlorine, bromine and methyl;

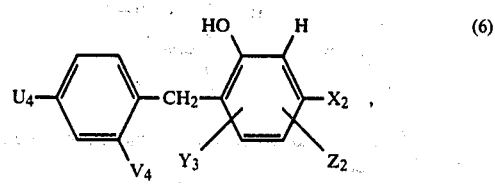

wherein $X_2$ and $Z_2$ have the meanings previously assigned to them, $Y_3$ represents hydrogen, chlorine or bromine, $U_4$ represents hydrogen, fluorine, chlorine or methyl, and $V_4$ represents hydrogen, fluorine, chlorine or methyl, and at least one of the substituents $Y_3$, $Z_2$, $U_4$ and $V_4$ represents one of the indicated halogens and at most one of the substituents $U_4$ and $V_4$ represents methyl:

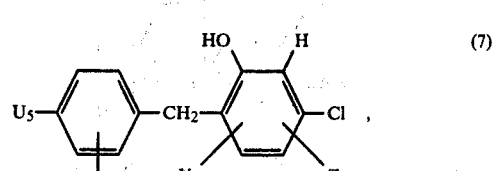

wherein $Z_2$ has the meaning previously assigned to it, $Y_3$ represents hydrogen, chlorine or bromine, $U_5$ represents hydrogen or chlorine and $V_5$ represents hydrogen or chlorine, and at least two of the substituents $Y_3$, $Z_2$, $U_5$ and $V_5$ represent chlorine and/or bromine;

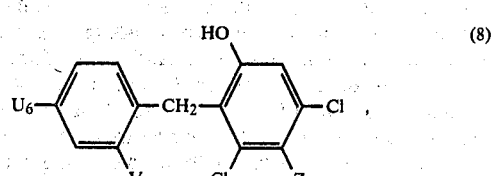

wherein one of the substituents $U_6$ and $V_6$ represents fluorine or chlorine and the other represents hydrogen and $Z_3$ represents hydrogen or chlorine, and

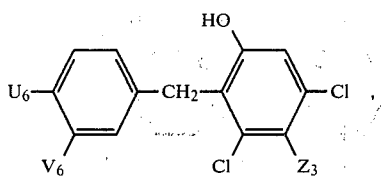

(8a)

wherein $U_6$, $V_6$ and $Z_3$ have the meanings previously assigned to them;

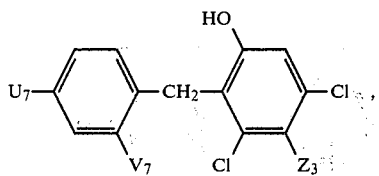

(8b)

wherein one of the substituents $U_7$ and $V_7$ represents hydrogen or chlorine, and

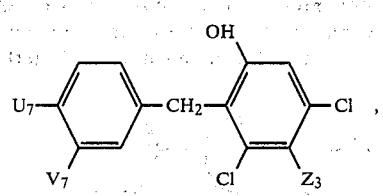

(8c)

wherein $U_7$, $V_7$ and $Z_3$ have the meanings previously assigned to them.

Preferred compounds of each of the formulae (1) to (6) are those with altogether 3 to 4 halogen atoms in the molecule.

The novel compounds of the formula (1) and of the related formulae can be manufactured by methods analogous to known ones. For example, they can be manufactured by reduction of ketones of the formula

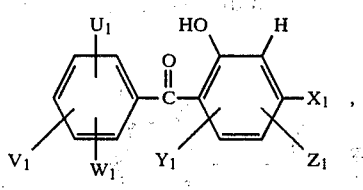

(9)

wherein $X_1$, $Y_1$, $Z_1$, $U_1$, $V_1$ and $W_1$ have the meanings previously assigned to them.

The reduction of the ketones can be carried out by various methods which are known in the art. Thus it is possible, for example, to use successfully the reduction method of Wolff-Kishner (cf. D. Todd, Organic Reactions 4, 378; 1943). This consists in converting the particular ketone firstly into the hydrazone and reducing this latter with sodium ethylate at elevated temperature and under pressure to the corresponding hydrocarbon. According to a modified process of Huang-Milon, Journal of the American Chemical Society 68, 2487; 1946), the decomposition of the hydrazone takes place in an inert solvent at elevated temperature—but at normal pressure—using an inorganic base. Advantageously the procedure to be followed is that the ketone is heated first in an inert, high-boiling, water-miscible solvent together with an excess of hydrazine hydrate and an alkali hydroxide to 100°–150° C., and then the resulting hydrazone, after the water and excess hydrazine hydrate have been distilled off, is decomposed by heating it to 180°–220° C.

Particularly good yields are obtained by using a glycol, e.g. ethylene glycol, diethylene glycol, or triethylene glycol, as solvent. It is advantageous to use sodium or potassium hydroxide as alkali hydroxide, as a rule in an amount of 6 to 14 moles per mole of ketone. The formation of the hydrazone succeeds best if the process is carried out at a temperature of 120°–140° C. with an excess of 6 to 14 moles of hydrazine hydrate per mole of ketone. The resulting hydrazone is decomposed most advantageously at a temperature between 190°–210° C. The reaction times required for the formation of the hydrazone are between 30 minutes and 3 hours, and those for the decomposition of the hydrazone between 1 and 5 hours.

The Clemmensen reduction (cf. Clemmensen, Berichte der deutschen Chemischen Gesellschaft 46, 1837; (1913) and 47, 51,681;(1914), also E. L. Martin, Journal of the American Society 58, 1438;(1936) is a further good method for manufacturing the benzylphenols according to the invention from the corresponding ketones. Here the reduction is carried out by heating the ketones with amalgamated zinc and hydrochloric acid, optionally in the presence of an organic solvent. Owing to the poor water-solubility of the ketones of the formulae (9), it is advantageous to carry out the reduction in the presence of water-miscible organic solvents, e.g. ethanol, acetic acid or dioxan.

It is, however, also possible to carry out the reaction in a two-phase system consisting ot the aqueous phase and a water-soluble solvent, e.g. benzene, toluene, or higher hydrocarbon.

The reaction temperature can vary between e.g. 20° C. and the boiling temperature of the solvent used. The reaction times are accordingly from 48 hours to 1 hour. Particularly good yields are obtained from the reduction by using 15 to 30 gram-atoms per mole of ketone to be reduced.

An electrochemical reduction of the carbonyl group at a lead cathode is also possible [L. Throop, L, Tökes, JACS 89, 4789 (1967)].

Another possible reduction method is the splitting by hydrogenation of the dialkylthioketals or ethylenethioketals manufactured from the ketones of the formula (9) with Raney nickel [cf. L. F. Fieser and W. Y. Huang, Journal of the American Chemical Society 75, 5356 (1953)].

The ketones of the formula (9) to be used as starting materials are known or they can be manufactured by methods that are known per se, e.g. from the corresponding phenyl benzoates by the Fries reaction (cf. Baltzly et al., Journal of the American Chemical Society, 77, 2522 (1955) or L. F. and M. Fieser, Lehrbuch der organischen Chemie 1954, page 728). The reaction can be carried out in the melt or in the presence of an organic solvent, e.g. nitrobenzene. The 2-hydroxybenzophenones of the formula (9) are then formed by heating the corresponding phenyl benzoate together with aluminium chloride.

Esters of the formula

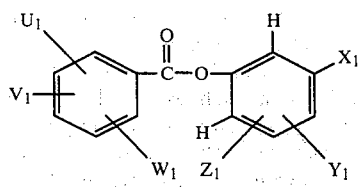

wherein $X_1$, $Y_1$, $Z_1$, $U_1$, $V_1$, and $W_1$ have the meanings previously assigned to them, undergo rearrangement in the Fries reaction for the manufacture of the compounds of the formula (9).

The compounds of the formula (10) are obtained by known methods, e.g. by reaction of a corresponding benzoyl halide with a corresponding phenol.

Further, it is also possible to manufacture the novel compounds in known manner by reaction of a phenyl halide of the formula

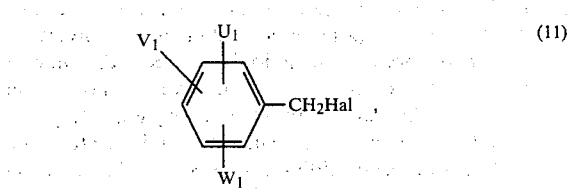

wherein Hal represents bromine or chlorine and $U_1$, $V_1$ and $W_1$ have the meanings previously assigned to them, with a phenol of the formula

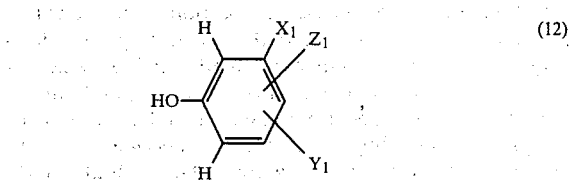

wherein $X_1$, $Y_1$ and $Z_1$ have the meanings previously assigned to them, under Friedl-Crafts conditions (cf. for example R. C. Histon, J.A.C.S. 46, 2775, 1924 and G. A. Olah, Friedel-Crafts and Related Reactions, Vol. II/I, 1964). The compounds of the formula (11) and (12) are known.

However, the novel o-benzylphenols can also be obtained by rearrangement from the corresponding benzyl ethers, e.g. with a catalytic amount of sulphuric acid at temperatures between 20° C. and 200° C. (V. V. Bailey-Wood and N. M. Cullinane, Chem. and Ind. 1959, 543) or with aluminium chloride at temperatures between −40° C. and +50° C. (St. Tarbell and J. C. Petropoulos, J.A.C.S. 74, 244, 1952) in an organic solvent. The benzyl ethers can be obtained by conventional methods from the benzyl halides of the formula (11) and the phenols of the formula (12).

The novel o-benzylphenols can also be obtained by reaction of benzyl ethers of the formula

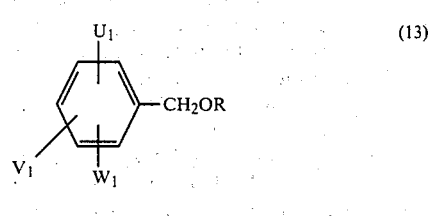

wherein $U_1$, $V_1$, and $W_1$ have the meanings previously assigned to them and R represents alkyl with 1 to 4, preferably 1 to 2, carbon atoms, with phenols of the formula (12) with the addition of an acid catalyst, e.g. $BF_3$ (cf. W. J. Monacelli and G. F. Hennion, J. Am. Chem. Soc. 63, 1722, 1941). The reaction can be carried out with or without a solvent at temperatures between 20° C. and 200° C. The benzyl ethers of the formula (13) can be obtained from the corresponding benzyl halides of the formula (11) (cf. J.A.C.S. 63, 1722, 1941).

As yet another method for manufacturing the novel compounds mention may be made of the after-halogenation of optionally substituted 2-benzyl-5-halogenophenols.

The compounds of the formula (1) have good sulubility in organic solvents and in propellant gases for aerosols. Their water-soluble salts, in particular the alkali and alkaline earth salts, are also effective and are of especial importance where an application in aqueous medium and in soaps is contemplated.

Particular importance attaches to the compounds of the formula (1) on account of their broad antibacterial activity spectrum which embraces both Gram-positive and Gram-negative bacteria, fungi as well as their substantivity for skin. With regard to the technical aspects of their use, the colourlessness and odourlessness of the novel compounds are of especial value.

The antimicrobial compounds of the present invention can be used on a very broad basis, in particular for protecting organic substrates from attack by harmful and pathogenic microorganisms. The antimicrobial agents are suitable accordingly as preservatives and disinfectants for industrial products of all kinds, as well as for deodorisation.

As examples of industrial products which can be preserved with the compounds of the formula (I) according to the invention the following may be mentioned: adhesive substances, binding agents, paints, textile assistants and finishing agents, oil pastes and printing pastes and similar preparation based on organic and inorganic dyestuffs and pigments, also those which contain casein or other organic compounds as admixtures. Wall and ceiling paints, for example those which contain an albuminous colour binder, are also protected from attack by pests by addition of the compounds according to the invention. Their use for protecting wood is also possible.

The compounds according to the invention can also be used as preservatives in the pulp and paper industry, inter alia for preventing the known formation of mucilage caused by microorganisms in the apparatus used for manufactuuring paper.

The action of the compounds according to the invention can also be utilized in providing plastics with preservative and disinfectant finishes. In the use of plasticisers it is advantageous to add the antimicrobial agent to the plastic in the plasticiser in dissolved or dispersed form. It is expedient to ensure as uniform a distribution in the plastic as possible. The plastics with antimicrobial properties can be used for commodities of all kinds in which an activity against bacilli of the most diverse kinds, for example bacteria and fungi, is desired, thus for example for foot mats, bathroom curtains, seating accomodation, steps in swimming baths, wall hangings etc. By incorporating the compounds according to the invention into corresponding wax compositions and floor polishing pastes there are obtained floor and furniture polishes with disinfectant action.

The compounds according to the invention are used with advantage for providing fibres and textiles with a preservative and disinfectant finish. They can be applied to natural and synthetic fibres on which they exert a lasting action against harmful (also pathogenic) microorganisms, for example fungi and bacteria. The compounds can be added before, simultaneously with, or after a treatment of these textiles with other substances, e.g. oil or printing pastes, flameproofing agents, fabric softeners, and other finishing agents. Textiles thus treated also have protection against perspiration odour caused by microorganisms.

The forms in which the active substances according to the invention are applied correspond to the usual formulations. The agents used for the finishing or for the protection of textiles should contain the active substances in a finely divided form. In particular, solutions, dispersions and emulsions of the active substances are therefore used. Aqueous dispersions can be obtained, for example, from pastes or concentrates, and can be applied as liquids or in the aerosol form.

The aqueous solutions or dispersions advantageously contain surface-active agents; for example, anionic compounds such as soaps and other carboxylates (e.g. alkali salts of higher fatty acids), derivatives of sulphur-oxyacids (e.g. sodium salt of dodecylbenzenesulphonic acid, water-soluble salts of sulphuric acid monoesters of higher molecular alcohols or of their polyglycol ethers, for example soluble salts of dodecyl alcohol sulphate or of dodecyl alcohol polyglycol ether sulphate), derivatives of phosphorusoxyacids (e.g. phosphates), derivatives with acid (electrophilic) nitrogen in the hydrophilic group (e.g. disulphine salts), cationic surface-active agents, such as amines and their salts (e.g. lauryldiethylenetriamine), onium compounds, amine oxides or nonionic surface active agents, e.g. polyhydroxy compounds, surface-active agents based on mono- or polysaccharide, higher molecular acetylene glycols, polyglycol ethers (e.g. polyglycol ethers of higher fatty alcohols, polyglycol ethers of higher molecular-alkylated phenols). In addition, the liquor can contain conventional adjuvants, for example water-soluble perborates, polyphosphates, carbonates, silicates, fluorescent brighteners, plasticisers, acid reacting salts, e.g. ammonium- or zincsilicofluoride, or certain organic acids, e.g. oxalic acid, also finishing agents, e.g. those based on synthetic resin or on starch.

The textile materials can be impregnated with the active substances, e.g. by means of hot or cold aqueous dyeing, bleaching, chroming or aftertreatment baths, whereby various textile-finishing processes are suitable, e.g. the padding or exhaustion process.

On account of their better solubility in organic solvents, the active substances are also suitable for application from non-aqueous media. The materials to be finished or preserved can moreover simply be impregnated with the solutions.

Suitable organic solvents are for example, trichloroethylene, methylene chloride, hydrocarbons, propylene glycol, methoxyethanol, ethoxyethanol or dimethyl formamide, to which may also be added dispersing agents (e.g, emulsifiers, such as sulphated castor oil, fatty alcohol sulphates, etc), and/or other auxiliaries.

Depending on the purpose of application, the content of active substances according to the present invention can be between 0.1 and 50 g. preferably between 1 and 30 g. of active substance per liter of treatment liquid.

The active substances according to the present invention can be used on their own, or together with other known antimicrobial textile-preserving agents.

Suitable textiles to be finished or preserved are both fibres of natural origin, such as cellulose-containing fibres, e.g. cotton, or polypeptide-containing fibres, e.g. wool or silk, and fibre materials of synthetic origin, such as those based on polyamide, polyacrylonitrile or polyester, as well as blends of these fibres.

In general the textile materials are adequately preserved against infestation by fungi and bacteria by a content of 0.01 to 5%, preferably 0.1 to 3%, of active substance, based on the weight of the textile materials.

Detergents and cleansing agents having excellent antibacterial or antimycotic action are obtained by combining the compounds according to the invention with interfacial-active substances, especially with active detergents.

The detergents and cleansing agents can be in any desired form, e.g. in liquid, pasty, solid, flake or granular form. The compounds according to the invention can be incorporated into anionic compounds, such as soaps and other carboxylates (e.g. alkali salts of higher fatty acids), derivatives of sulphur-oxyacids (e.g. sodium salt of dodecylbenzenesulphonic acid, water-soluble salts of sulphuric acid monoesters of higher-molecular alcohols or of their polyglycol ethers, for example soluble salts of dodecyl alcohol sulphate or of dodecyl alcohol polyglycol ether sulphate), derivatives of phosphorusoxyacids (e.g. phosphates), derivatives with acid (electrophilic) nitrogen in the hydrophilic group (e.g. disulphine salts), as well as into cationic surface-active agents, such as amines and their salts (e.g. lauryldiethylenetriamine), onium compounds, amine oxides or nonionic surface-active agents, such as polyhydroxy compounds, surface-active agents based on mono- or polysaccharide, higher-molecular acetylene glycols, polyglycol ethers (e.g. polyglycol ethers of higher fatty alcohols, polyglycol ethers of higher-molecular alkylated phenols), or into mixtures of different surfactants. The antimicrobial activity of the new compounds is therewith completely retained. The active substance content of the detergents and cleansing agents, based on the weight of this agent, is generally from 0.01 to 5%, generally 0.1 to 3%. Aqueous preparations of such detergents and cleansing agents containing compounds according to the invention can be employed, for example, for the antimicrobial finishing of textile materials, since the active substance can be absorbed substantively on to the textile material. They are also suitable as antimicrobial cleansing agents in the food manufacturing and bottling industries, e.g. in breweries, dairies, cheese dairies and slaughterhouses.

Furthermore, the compounds according to the invention can also be used in cosmetic preparations, e.g. volatile oils, bath salts, brilliantines, ointments, face lotions, hair-dyeing preparations, hair oils, hair tonics, skin creams, skin oils. Eau-de-Cologne, perfumes, powders, rouge, depilatorics, sun-ray filter creams, dental hygiene products, etc., in consequence of which there is additionally imparted to these products in antimicrobial and deodorant action. In general, an active-substance content, based on the total weight of the product, of 0.01 to 5%, preferably of 0.1 to 3%, suffices.

For the purpose of disinfection and preservation, the compounds of formula I can also be used in combination with known antimicrobial agents. These include, e.g.:

Halogens and Halogen Compounds with Active Halogen e.g. sodium hypochlorite, calcium hypochlorite, chloride of lime, sodium-p-toluenesulphochloramide, p-toluenesulphodichloramide, N-chlorosuccinimide, 1,3-dichloro-5,5-dimethyl-hydantoin, trichloroisocyanuric acid, potassium-dichloroisocyanurate, iodine, iodine trichloride, complex compounds of iodine and iodine trichloride with surface-active agents such as polyvinylpyrrolidone, alkylphenoxypolyglycols, polyoxypropylene glycols, alkylaminoethanesulphonic acids and -sulphonates, alkylarylsulphonates, quaternary ammonium compounds.

Boron Compounds e.g boric acid, borax.

Organometallic Compounds e.g. bis-tributyltin oxide, triphenyltin hydroxide, tributyltin salicylate, tributyltin chloride, phenyl-mercury borate, phenylmercury acetate.

Alcohols e.g hexyl alcohol, trichloroisobutyl alcohol, 1,2-propylene glycol, triethylene glycol, benzyl alcohol, 4-chlorobenzyl alcohol, 2,4- and 3,4-dichlorobenzyl alcohol, 2-phenylethyl alcohol, 2-(4-chlorophenyl)-ethyl alcohol, ethylene glycol monophenyl ether, methanol, linalool and 2-bromo-2-nitro-propanediol-1,3.

Aldehydes e.g. formaldehyde, paraformaldehyde, glutaraldehyde, benzaldehyde, 4-chlorobenzaldehyde, 2,4- and 3,4-dichlorobenzaldehyde, cinnamaldehyde, salicyclic aldehyde, 3,5-dibromosalicylic aldehyde, 4-hydroxybenzaldehyde, anisaldehyde and vanillin.

Carboxylic Acids and Derivatives e.g. trichloroacetic acid, monobromoacetic acid glycol ester, Na- and Ca-propionate, caprylic acid, undecylonic acid, En-undecylenate, sorbic acid, K- and Ca-sorbate, lactic acid, malonic acid, aconitic acid, citric acid, benzoic acid, 4-chlorobenzoic acid, benxoic acid benzyl ester, salicylic acid, 4-chlorosalicylic acid-n-butylamide, salicylanilide, 3,4',5-tribromosalicylanilide, 3,3',4'-tetrachlorosalicylanilide, 4-hydroxybenzoic acid, 4-hydroxybenzoic acid ethyl ester, gallic acid, mandelic acid, phenylpropionic acid, phenoxyacetic acid, dehydracetic acid and vanillic acid propyl ester.

Phenols e.g. phenol, mono- and polychlorophenols, cresols, 4-chloro-3-methylphenol, 4-chloro-3,5-dimethylphenol, thymol, 4-chlorothymol, 4-t-amylphenol, saligenin, 4-n-hexylresorcin, carvacrol, 2-phenylphenol, 2-benzyl-4-chlorophenyl, 2,2'-dihydroxy-5,5'-dichlorodiphenylmethane, 2,2'-dihydroxy-3,3',5,5',6,6'-hexachloro-diphenylmethane, 2,2'-dihydroxy-5,5'-dichloro-diphenylsulphide, 2,2'-dihydroxy-3,3',5,5'-tetrachlorodiphenylsulphide, 2-hydroxy-2',4,4'-triichlorodiphenyl ether and dibromosalicyl.

Quinones e.g. 2,5-dimethylquinone, 2,3,5,6-tetrachloro-benzoquinone, 1,4-2,3-dichloro-1,4-naphthoquinone.

Carbonic Acid Derivatives e.g. pyrocarbonic acid diethyl ester, tetramethylthiuram disulphide, 3,4,4'-trichloro-N,N'-diphenylurea, 3-trifluoromethyl-4,4'-dichloro-N,N'-diphenylurea, N-3-trifluoromethylphenyl-N'-2-ethylhexyl-urea, 1,6-bis-(4'-chlorophenyl-di-guanidino)-hexane, dodecylmethyl-guanidine acetate, ammonium rhodanide, 4,4'-diamino-α,ω-diphenoxy-hexane.

Amines e.g. dodecylpropylenediamine, dodecyldiethylene-triamine and diaminobenzene-dihydroiodide.

Quaternary Ammonium Compounds e.g. alkyl-dimethyl-benzyl-ammonium chloride, alkyldimethyl-ethyl-benzyl-ammonium chloride, dodecyl-dimethyl-3,4-dichlorobenzyl-ammonium chloride, dodecyl-di-(2-hydroxyethyl)-benzyl-ammonium chloride, dodecyl-di-(2-hydroxyethyl)-benzyl-ammonium-pentachlorophenolate, dodecyl-di-(2-hydroxyethyl)-benzyl-ammonium-4-methyl benzoate, dodecyl-dimethyl-phenoxyethyl-ammonium bromide, 4-diisobutyl-phenoxyethoxyethyl-dimethyl-benzyl-ammonium chloride, 4-diisobutyl-cresoxyethoxyethyl-dimethyl-benzyl-ammonium chloride, dimethyl-didecyl-ammonium chloride, cetyltrimethylammonium bromide, dodecyl-pyridinium chloride, cetyl-pyridinium chloride, dodecyl-isoquinolinium chloride, decamethylene-bis-4-aminoquinaldinium dichloride, α-(p-tolyl)-dodecyl-trimethyl-ammonium methosulphate, (dodecanoyl-N-methyl-aminoethyl)-phenylcarbamoyl-methyl)-dimethyl-ammonium chloride.

Quaternary Phosphonium Compounds e.g. dodecyl-triphenyl-phosphonium bromide.

Amphoteric Compounds e.g. dodecyl-di-(aminoethyl)-glycine.

Heterocyclic Compounds e.g. 2-mercaptopyridine-N-oxide, Na- and Zn-salt of 2-mercaptopyridine-N-oxide, 2,2'-dithiopyridine-1,1'-di-N-oxide, 8-hydroxyquinoline, 5-chloro-8-hydroxyquinoline, 5-chloro-7-iodine-8-hydroxyquinoline, 5,7-dichloro-8-hydroxyquinoline, 5,7-dichloro-8-hydroxyquinaldine, bis-2-methyl-4-amino-quinolyl-carbamide-hydrochloride, 2-mercaptobenzthiazle, 2-(2'-hydroxy-3',5'-dichlorophenyl)-5-chlorobenzimidazole, 2-aminoacridine-hydrochloride, 5,6-dichlorobenzoxazolone, 1-dodecyl-2-iminoimidazolinehydrochloride and 6-chloro-benzisothiazolone.

The applicability of compounds of formula (1) for combating microorganisms, particularly bacteria and fungi, and for preserving organic materials and objects from infestation by microorganisms, is very extensive. Thus, for example, they can be incorporated direct into the material to be preserved, e.g. into material having a synthetic resin base, such as polyamides and polyvinyl chloride, into paper-treatment liquors, into printing thickeners made from starch or cellulose derivatives, into lacquers and paints which contain, for example, casein, into cellulose, viscous spinning solutions, paper, into animal mucus or oils, into permanent coatings based on polyvinyl alcohol, cosmetic articles, and into ointments or powders. They can also be added to preparations of inorganic or organic pigments for the paint industry, to plasticisers, etc.

The compounds of formula I can be used furthermore in the form of their organic solutions, e.g. as sprays, or as dry-cleaning agents, or for the impregnation of wood; suitable organic solvents being preferably solvents immiscible with water, particularly petroleum fractions, but also solvents miscible with water, such as lower alcohols, e.g. methanol or ethanol or ethylene glycol monomethyl ether, or -monoethyl ether. Some of the new compounds can be used also in aqueous solution.

Furthermore, they can be used together with wetting or dispersing agents, in the form of their aqueous dispersions, e.g. for the preservation of substances which tend to rot, for example for the preservation of leather, paper etc., since they undergo a slighter deactivation through wetting agents and dispersants.

Solutions or dispersions of active substances, which can be used for the preservation of these materials, preferably have an active-substance content of at least 0.005 g/liter, e.g. 0.01 to 5, preferably 0.1 to 3 g/liter.

The compounds of the present invention also have an excellent growth-promoting action in productive livestock, e.g. pigs and poultry, as well as ruminants, such as cattle or sheep.

The active substances can be administered to the animals perorally or via the abomasum, or by means of injection, in the form of solutions, emulsions, suspensions, powders, tablets, boluses and capsules, either as a single dose or as repeated doses. The active sustances or mixtures containing them may also be added to the feed or to the drinking through, or they can be contained in so-called premixes.

By virtue of their wide microbiocidal activity spectrum, the compounds of the present invention can also be used in veterinary medicine for the control of pathogenic microorganisms on and in animals, particularly on the skin and in the intestinal tract and urogenital system. For the control of pathogenic microorganisms in veterinary medicine and/or the attainment of a growth-promoting action in productive livestock, the compounds of the present invention can be combined with the following substances.

1. Antibiotics
   penicillin and its derivatives,
   cephalosporin and its derivatives,
   chloramphenicol,
   tetracyclines (e.g. chlorotetracycline, oxytetracycline),
   rifamycin and its derivatives (e.g. Rifampin)
   lincomycin
   bacitracin and its salts,
   pyrrolnitrin,
   myxin,
   streptomycin,
   nigericin,
   parvulin,
   spiramycin,
   neomycin,
   thiopeptin,
   tylosin.
2. Sulphonamides
   N'-(3,4-dimethyl-5-isoxazolyl)-sulphanilamide,
   N'-2-pyrazinylsulphanilamide,
   2,4-dimethoxy-6-sulphamylamino-1,3-diazine,
   N'-(4-methyl-2-pyrimidyl)-sulphanilamide.
3. Nitrofurans
   3-(5-nitrofurfurylideneamino)-2-oxazolidinone,
   5-morpholinomethyl-3-(5-nitrofurfurylideneamino)-2-oxazolidinone,
   3-amino-6-[2-(nitro-2-furyl)vinyl]-pyridazine,
   1,5-di-(5'-nitro-2'-furyl)-penty-1,4-dien-one-(3)-2"-amidinohydrazone-hydrochloride.
4. Diaminopyrimidines
   2,4-diamino-5-(3,4,5-trimethoxybenzyl)-pyrimidine,
   2,4-diamino-5-(3,4-dimethoxybenzyl)-pyrimidine,
   2,4-diamino-5-(p-chlorophenyl)-6-ethylpyrimidine.
5. Hydroxyquinolines
   5,7-dichloro-8-hydroxyquinaldine,
   5-chloro-7-iodo-8-hydroxyquinoline.
6. Hydroxyquinolinecarboxylic acids and hydroxynaphthyridine acids
   1-ethyl-1,4-dihydro-7-methyl-4-oxo-1,8-napthyridine-3-carboxylic acid,
   oxolinic acid.
7. Quinoxaline-di-N-oxides
   quinoxaline-1,4-di-N-oxide,
   3-(1,4-dioxo-2-quinoxalinemethylene)-carbazinic acid methyl ester.
8. Halogenated hydroxydiphenyl ethers
   2-hydroxy-2',4,4'-trichloro-diphenyl ether.
9. Nitrohydroxydiphenyl ethers
10. Optionally halogenated salicyclic acid anilides
11. Triarylmethylimidazoles
    di-(phenyl)-2-chlorophenyl-imidazolyl(1)-methane.
12. Vitamins.
13. 3-Hydroxy-2-methyl-4-pyrone.
14. 2-Mercaptoimidazole.
15. Ethoxylated alcohols:
    such as $R-O(CH_2CH_2O)_nH$.
16. 2-Bromo-5-nitrothiazole
17. Guanidines
18. N-Substituted aminoacetic acids
19. β-Nitropropionic acid
20. Phenylcyclopropylamine
21. 2-(4-Thiazolyl)-benzimidazole
22. Piperazine and its salts
23. Benzodiazepinone derivatives
24. Dihydroxydiphenylsulphides
25. 4,5-Dihydroxy-2,4,6-octatrienedicarboxylic acids
26. 2-Formyl-4-chlorophenoxyacetic acids
27. Straight-chain aliphatic alcohols
28. 2-Chloro-10-(3-dimethylaminopropyl)-phenothiazine
29. Acetoxybenzoic acid
30. Auxins
    3,5-di-sec.butyl-α,β,γ-trihydroxy-1-cyclopentenevaleric acid,
    3,5-di-sec.butyl-γ-hydroxy-β-oxo-1-cyclopentenevaleric acid.

Besides having a good microbicidal action, the compounds of the present invention have a good anthelmintic action. In therapeutically effective doses, they are excellently compatible, and are outstandingly effective against:

Helminths nematodes, such as ascaridae, trichostrongylidae ancylostomatidae or stronglylidae;
cestodes, such as anoplocephalidae, taenidae, trematodac and faciolidae.

The agents containing the active substances of formula (I) according to the invention can be used for the control of parasitic helminths in domestic animals and productive livestock, e.g. cattle, sheep, goats, horses, pigs, cats, dogs and poultry. They can be administered to the animals both as a single dose or as repeated doses, the single doses being preferably between 25 and 1000 mg of active substances per kg of body weight, depending on the species of animal. An improved action is obtained in some cases by a protected administration, or similar overall doses may suffice. The active substances or mixtures containing them can also be added to the feed or the drinking through. The prepared feed contains the substances of formula (I) preferably in a concentration of ca. 0.005 to 1 percent by weight.

EXAMPLE 1

87.5 g of chlorobenzoyl chloride and 81.5 g of dichlorophenol are stirred for 1½ hours in a current of nitrogen at 145° C. While splitting off hydrogen chloride the product of the formula

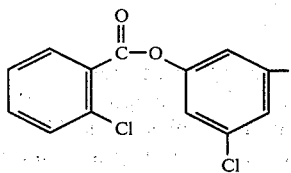
(14)

is formed virtually quantitatively. Without isolation of the ester of the formula (14), 150 g of aluminium chloride are added at 140° C. to 150° C. After the reaction mixture has been stirred for 2½ hours at 180° C. to 190° C., it is cooled to 150° C. and then 100 ml of chlorobenzene are added. The solution is poured on ice and the chlorobenzene is removed by steam distillation. The product is collected by suction filtration and dried in vacuo at 160° C. Yield: 139 g. The product is dissolved in a hot cyclohexane/hexane mixture, the solution is treated with a small amount of activated charcoal, filtered clear and allowed to cool, to yield 85 g of the compound of the formula

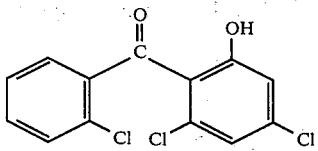
(15)

in the form of colourless crystals with a melting point of 71° C. to 73° C.

A mixture of 60.3 g of the compound of the formula (15), 60 g of hydrazine hydrate and 67.2 g of potassium hydroxide is heated for 3 hours to 140° C. in diethylene glycol. Thereafter water and surplus hydrazide are distilled off, the temperature rising slowly to 195° C. The contents are then poured on ice and the resultant solution is adjusted to a pH of 2 with dilute hydrochloric acid. The precipitated oil is extracted with benzene and the benzene solution is washed in water, dried with sodium sulphate and finally evaporated. The oily residue crystallises after a time by itself. It is dissolved hot in a mixture of hexane and cyclohexane and is seeded after it has cooled to yield 30 g of the compound of the formula

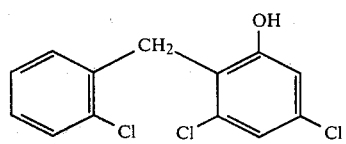
(16)

in the form of colourless crystals wit a melting point of 78° C.

The compounds of the general formula

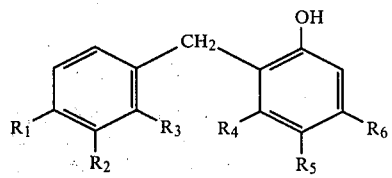
(17)

listed in the following Table are obtained in analogous manner.

| Compound | $R_1$ | $R_2$ | $R_3$ | $R_4$ | $R_5$ | $R_6$ | melting-/boiling temperature in °C. |
|---|---|---|---|---|---|---|---|
| 18 | Cl | H | H | Cl | H | Cl | 81 |
| 19 | Cl | Cl | H | Cl | H | Cl | 73–79 |
| 20 | H | H | H | Cl | H | Cl | 46–47 |
| 21 | Cl | H | H | H | Cl | Cl | 110–111 |
| 22 | Cl | H | H | H | H | Cl | 69–70 |
| 23 | H | H | H | H | H | Cl | <40 |
| 24 | Cl | Cl | H | H | H | Cl | 65 |
| 25 | Cl | H | Cl | H | H | Cl | 63–64 |
| 26 | H | H | $CH_3$ | Cl | H | Cl | 103–104 |
| 27 | H | H | H | H | Cl | Cl | <30 |
| 28 | H | Cl | H | Cl | H | Cl | bp$_{0.05}$ 145–150 |
| 29 | H | Cl | H | H | Cl | Cl | bp$_{0.05}$ 138–142 |
| 30 | H | H | Cl | H | Cl | Cl | 90–91 |
| 31 | H | H | Br | Cl | H | Cl | 99–102 |
| 32 | H | Br | H | Cl | H | Cl | 57–59 |
| 33 | Cl | H | H | H | Br | Cl | 112–115 |
| 34 | $CH_3$ | H | H | Cl | H | Cl | 36–87 |
| 35 | H | $CH_3$ | H | Cl | H | Cl | 62–64 |
| 36 | Cl | H | Cl | H | Br | Cl | 85–88 |
| 37 | Br | H | H | Cl | H | Cl | 103–104.5 |
| 38 | Cl | H | H | H | $CH_3$ | Cl | 71–72 |
| 39 | Cl | Cl | H | H | $CH_3$ | Cl | 85–86.5 |
| 40 | H | H | H | Br | H | Br | bp$_{0.05}$ 145–150 |
| 41 | Cl | H | H | Br | H | Br | 95.5–96.5 |
| 42 | H | H | H | H | Br | Cl | bp$_{0.05}$ 121–128 |
| 43 | Cl | H | Cl | H | Br | Cl | 85–88 |

EXAMPLE 2

104.8 g of 2,4-dichlorobenzoyl chloride and 81.5 g of 3,5-dichloropehnol are stirred for 1½ hours in a current of nitrogen at 145° C. While splitting of hydrogen chloride the product of the formula

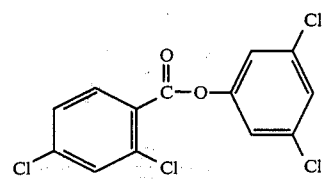
(44)

is formed quantitatively. Over the course of 10 minutes, 150 g of aluminium chloride are added to the product at 140° C. to 150° C. After the reaction mixture has been stirred for 2½ hours at 180° C. to 190° C., it is cooled to 150° C. and then 100 ml of chlorobenzene are added.

The still hot solution is poured on ice and the chlorobenzene is removed by steam distillation. After suction, filtration and drying at 60° C. the yield is 197 g of product. The product is dissolved in a hot cyclohexane/hexane mixture, the solution is treated with a small amount of activated charcoal, filtered, clear and allowed to cool, to yield 111.2 g of the product of the formula

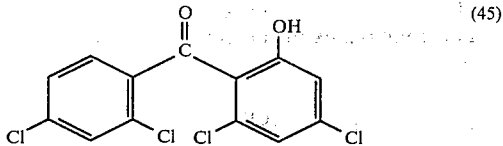
(45)

in the form of colourless crystals with a melting point of 107° C. to 108° C. 75 g of zinc powder are stirred for 5 minutes in a solution of 150 ml of 5% mercury (II) chloride and 4 ml of conc. hydrochloric acid. The zinc is then filtered off and added moist to a mixture of 115 ml of conc. hydrochloric acid, 63 ml of water, 12.5 ml of glacial acetic acid and 75 ml of toluene. While stirring, 42 g of the product of the formula (45) are added to the mixture, which is then heated to reflux for 26 hours. Every 6 hours 25 ml of conc. hydrochloric acid are added. After the reaction mixture has cooled, 600 ml of water are added and the two liquid phases are decanted off from the remaining zinc and extracted with 200 ml of benzene twice. The organic phases are washed neutral with water, dried with sodium sulphate and evaporated. The residual oil crystallises after a few days by itself. The solid product is dissolved hot in a mixture of cyclohexane/hexane and the solution is filtered clear after addition of a small amount of activated charcoal. After cooling there are obtained 24 g of the product of the formula

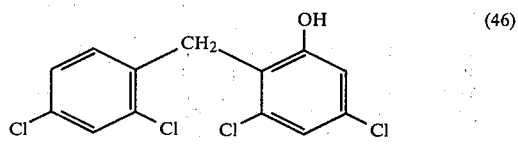
(46)

in the form of colourless crystals wit a melting point of 70° C. to 71° C. The compounds of the formula

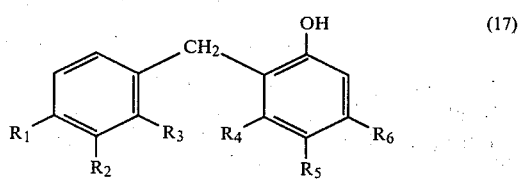
(17)

listed in Table 2 are obtained in analogous manner.

TABLE 2

| Compound | $R_1$ | $R_2$ | $R_3$ | $R_4$ | $R_5$ | $R_6$ | melting point and boiling temperature in °C. |
|---|---|---|---|---|---|---|---|
| 47 | F | H | H | Cl | H | Cl | 59–60 |
| 48 | H | H | F | Cl | H | Cl | 56–57 |
| 49 | H | F | H | Cl | H | Cl | 50–51 |
| 50 | F | H | H | H | Cl | Cl | 60–61 |
| 51 | $CH_3$ | Cl | H | Cl | H | Cl | |
| 52 | $CH_3$ | Cl | H | H | Cl | Cl | |

The compounds of the formula (16) and (18) to (43) can also be manufactured by this process.

EXAMPLE 3

16.1 g of sodium are dissolved in 200 ml of anhydrous ethyl alcohol and the solution is cooled to 5° C. Over the course of 30 minutes, 136.8 g of 3,4-di-chlorobenzyl chloride are added dropwise at 10° C. to 15° C. The mixture is stirred for 1 hour at room temperature and for 1 hour at reflux temperature. After it has cooled to 0° C., the solution is freed from precipitated sodium chloride and concentrated. The residue is distilled in vacuo to yield 127 g the product of the formula

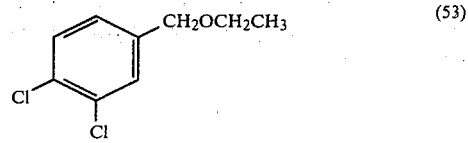
(53)

with a boiling point of 123° C. to 126° C.

A mixture of 41 g of the compound of the formula (53), 49 g of 3,4,5-trichloro-phenol and 11.3 g of boron trifluoride etherate (48%) is heated for 4 hours to 100° C. with stirring. The mixture is cooled, poured on ice and extracted with benzene. The benzene phase is washed neutral, dried and evaporated. The residue is distilled in vacuo to yield 24 g of the compound of the formula

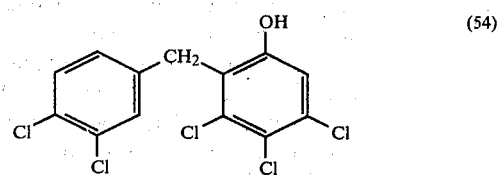
(54)

with a boiling point of 180° C. to 190° C. Recrystallisation from cyclohexane yields the compound of the formula (54) in the form of colourless crystals with a melting point of 130° C.–131° C. The compounds of the formula

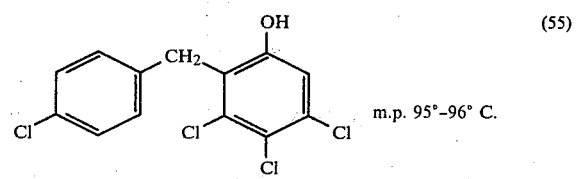
(55) m.p. 95°–96° C.

and

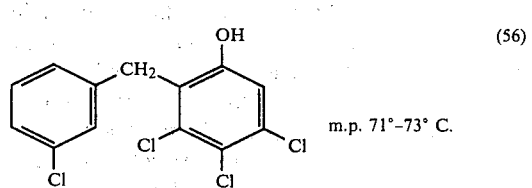
(56) m.p. 71°–73° C.

are obtained in analogous manner.

EXAMPLE 4

23 g of sodium are dissolved in 300 ml of anhydrous ethyl alcohol and reacted under the same conditions as described in Example 3 with 161 g of p-chloro-benzyl chloride. Yield: 149 g of the compound of the formula

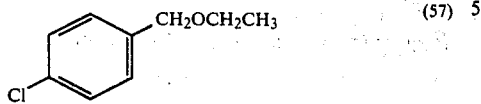 (57)

with a boloing point of 105°–107° C.

A mixture of 34.1 g of the compound (57), 65 g of 3,4-dichlorophenol and 11 g of boron trifluoride etherate (48%) is heated for 2 hours to 100° C. with stirring. The mixture is cooled, poured on ice and extracted with benzene. The benzene phase is washed neutral, dried and evaporated. The residue is distilled in vacuo to yield 40 g of an isomeric o-benzylphenol mixture with a boiling point of 134°–144° C. and consisting of 52.2% by weight of the compound

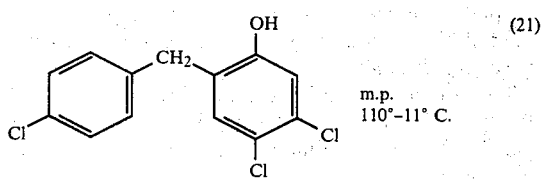 (21)

m.p. 110°–11° C.

and of 47.8% by weight of the compound

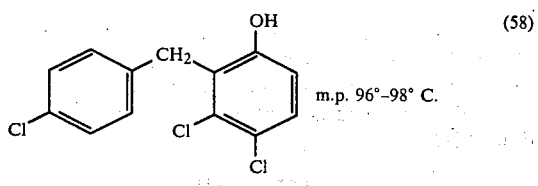 (58)

m.p. 96°–98° C.

The following isomeric mixtures can also be obtained in analogous manner:

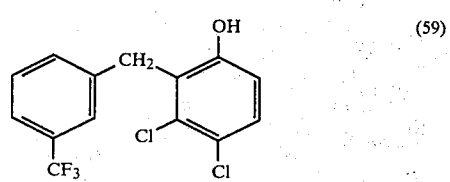 (59)

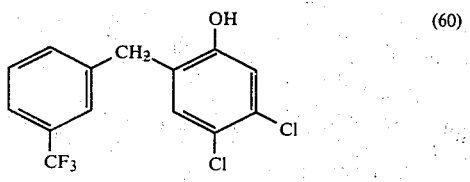 (60)

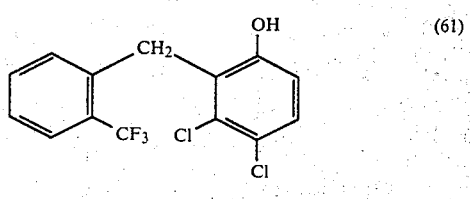 (61)

-continued

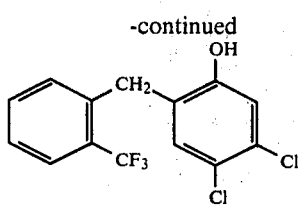 (62)

Analogous binary mixtures in each of which one component is one of the compounds listed in Tables 1 and 2 and wherein $R_4$ represents hydrogen and $R_6$ represents chlorine, can be manufactured from the corresponding benzyl ethers and 3,4-dichlorophenol.

EXAMPLE 5

With stirring 34.1 g of benzyl ether of the formula (57), 65 g of 3,5-di-chlorophenol and 11 g of boron trifluoride etherate (48) % are heated while stirring for 2 hours to 100° C. The mixture is cooled, poured on ice and extracted with benzene. The benzene phase is washed neutral, dried and evaporated. The residue is distilled in vacuo to yield 18 g of an isomeric mixture of benzylphenols (b.p. 0.05, 142°–146° C.) which consists of 85% of the compound of the formula (18) and 15% of the compound of the formula

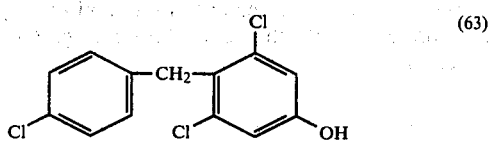 (63)

Analogous binary mixtures in which the principal component is a compound of Table 1 or 2 can be obtained from corresponding benzyl ethers and 3,5-dichloro-phenol. Only the compounds of Tables 1 and 2 wherein $R_4$ and $R_6$ represent chlorine and $R_5$ represents hydrogen are suitable as mixture component.

EXAMPLE 6

The compound of the formula (16), (18) to (43), (46), (47) to (52), (54) to (56) and (58) to (62) are dissolved in a suitable formulation (methyl cellosolve/dimethyl formamide). The formulations are incorporated into a nutrient agar solution and the inhibition of the growth of microorganisms are determined by the gradient test. Test microorganisms used:
Staph. aureus SG 511
Staph. aureus ATCC 13709
Staph. aureus M 6
Str. faccalis ATTCC 10541
Str. agalactine M 100
Bac. subtilis ATCC 6633
Escherichia coli NCTC 8195
Escherichia coli RP 45510, airsacculitis
Escherichia coli 205 CN 343
Escherichia coli M 155
Bord. bronchiseptica TSA 742
Past. multocida K 753
Proteus vularis ATCC 9484
Salm. pullorum VBIZ
Salm. typhimurium K 1079
Pseudomonas aeruginosa ATTCC 10145
Pseudomonas aeruginosa NCTC 8060
Pseudomonas solanaccarum 504
Pseudononas lachrymans 545

Xanthomonas vesicatoria 555
Erwinia salicis 600
Erwinia tracheiphila 610
Erwinia carbtovora 604
Candide albicans ATTCC 10259
Candida albicans H 500
Trich. mentagrophytes ATCC 9533
Asp. elegans H 3637
Staph. aurcus SG 511
Clostr. perfringens La 935

Gradient plate test

Preparation of the test plates according to the scheme

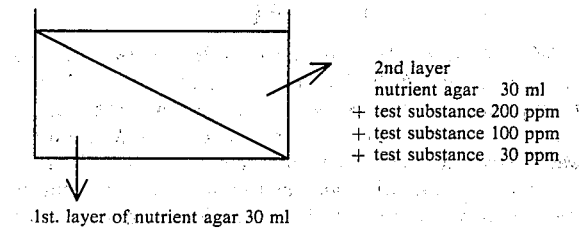

1st. layer of nutrient agar 30 ml

2nd layer
nutrient agar   30 ml
+ test substance 200 ppm
+ test substance 100 ppm
+ test substance  30 ppm Drying of the gradient plates in circulating air incubator.

Inoculation with organisms or spore suspensions by application of a germ band with a capillary pipette in the direction of the concentration gradient (see scheme).

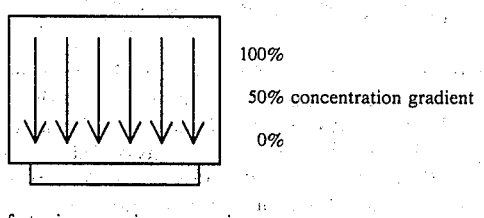

100%
50% concentration gradient
0% fast microorganism suspension

Incubation of the plates inoculated with bacteria and fungi for 24 to 36 hours at 37° C.

Nutrient agar: bactoria: nutrient agar
fungi: Sabourad-Maltose agar

The compounds of the formula (16), (18) to (43), (46), (47) to (52), (54) to (56) and (58) to (62) exhibit good action against the bacteria and fungi used.

EXAMPLE 7

The compounds of the formula (16), (18) to (43), (46), (47) to (52), (54) to (56) and (58) to (62) are dissolved in a suitable formulation (ethyl collosolve/dimethyl formamide). The three substrates listed below are put into the formulation baths and subsequently squeezed out between 2 aluminium sheets. The substrates are then dried in the air. The squeezing is carried out in such a way that in case (a) 2500 ppm, (b) 250 ppm or (c) 25 ppm of active substances are present on the fabric.

1. Reinforced cotton, causticised, bleached, weight per m²: 121 g.

2. Polyamide, nylon staple fabric, fixed, bleached, weight per m²: 140 g.

3. Polyester, "Dacron" staple fabric, type 54, fixed, bleached, weight per m²: 130 g.

The substrates are then tested against the following 7 test organisms according to the agar diffusion test (modified AATC test method 90, 1970):

Bacteria

Staphylococcus aureus ATCC 6538
Esclerichia coli NCTC 8196
Proteus mirabilis NCTC 8309
Pseudomonas aeruginosa NCTC 8060

Fungi

Candida albicans ATCC 10'259
Trichophyton mentagrophytes ATCC 9533
Aspergillus niger ATCC 6275

The test plates consist of a twin layer agar, i.e. of a base layer of uninoculated nutrient agar and a surface layer of inoculated nutrient agar.

Bacteria: nutrient agar
Fungi: mycophil agar

The filtered microorganism suspension is poured on a congealed base layer and after the inoculated layer has congealed, paper discs of 20 mm diameter are placed on the treated substrates. The bacteria and candida plates are incubated for 24 hours at 37° C.; the fungi plates are incubated for 3 to 4 days at 28° C. After the incubation the plates are evaluated for inhibition zones. If there are no inhibition zones, the growth beneath the test samples is examined under a magnifying glass.

The compounds of the formula (16), (18) to (43), (46), to (47) to (52), (54) to (56) and (58) to (62) tested in this manner exhibit, in conjunction with the substrates used, good action against bacteria and fungi, for example Staphylococcus aureus, Proteus mirabilis, Candida albicans, Trichophytone mentagrophytes.

EXAMPLE 8

The compounds of the formula (16), (18) to (43), (46), (47) to (52), (54) to (56) and (58) to (62) are incorporated together with soap into a nutrient medium and the activity is determined according to the Agar Incorporations Test.

Microorganisms

1. Staph. aureus ATTCC 6538
2. Streptococcus faccalis ATTCC 10541
3. Corynebact. minutissimum NCTC 10288
4. Esch. coli NCTC 8196
5. Salmonella typhimurium NCTC 5710
6. Pseudo. aeruginosa NCTC 8060
7. Candida albicans ATTCC 10259
8. Trichophyton mentagrophytes ATCC 9533.

Nutrient media for 1 to 6: tryptone-glucose extract agar nutrient media for 7 and 8: Mycophil agar A 0.5% solution is prepared with sterilised water from a base soap compound, Sufficient of this stock solution is given to hot, sterile, liquid agar so that the nutrient medium contains 500 ppm soap.

The test substances are dissolved in dimethyl sulphoxide, content 500 ppm. The active substance solution is put into sterilised Petri dishes in amounts of 0.1, 0.05 and 0.01 ml and treated and toroughly mixed with 10 ml of nutrient medium which contains 500 ppm of soap (thus 5, 2.5 and 0.5 ppm are mixed in the nutrient medium).

After the plates have congealed the microorganism suspensions are dropped thereon with a Pasteur pipette or with an inoculation device. Microorganisms 1 to 4 are incubated for 24 hours at 37° C. and microorganism 5 is incubated for 5 days at 28° C. In this way it is determined whether the bacilli have grown or not. The compounds tested in this manner exhibit good activity against the microorganisms used.

What we claim is:

1. An o-benzylphenol of the formula

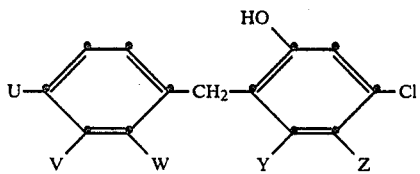

wherein
Y represents hydrogen or chlorine
Z represents hydrogen, chlorine or bromine,
U represents hydrogen, chlorine or fluorine,
V represents hydrogen or chlorine and
W represents hydrogen or chlorine.

2. An o-benzylphenol of claim 1, wherein at least one of U, V and W represents chlorine.

3. An o-benzylphenol of claim 1, wherein U represents chlorine and V and W represent hydrogen.

4. A compound of claim 1, which is 2-(4'-fluorobenzyl)-3,5-dichlorophenol.

5. A compound of claim 1, which is 2-benzyl-3,5-dichlorophenol.

6. A compound of claim 1, which is 2-(4'-fluorobenzyl)-4,5-dichlorophenol.

7. A compound of claim 1, which is 2-(3',4'-dichlorobenzyl)-5-chlorophenol.

8. A compound of claim 1, which is 2-(2',4'-dichlorobenzyl)-5-chlorophenol.

9. A compound of claim 1, which is 2-(2',4'-dichlorobenzyl)-4-bromo-5-chlorophenol.

10. A compound of claim 1, which is 2-(4'-chlorobenzyl)-4-bromo-5-chlorophenol.

11. A compound of claim 1, which is 2-(4'-chlorobenzyl)-4,5-dichlorophenol.

12. A compound of claim 1, which is 2-(4'-chlorobenzyl)-3,5-dichlorophenol.

13. A microbiocidal composition for combating harmful bacteria and fungi which comprises a bactericidally or fungicidally effective amount of at least one of the compounds of claim 1 and an inert carrier therefor.

14. A composition according to claim 13 which, in addition to the active substance, comprises at least one of the following additives as solid or liquid carrier: soaps, surface-active substances, foaming agents, emulsifiers, dispersants or wetting agents, water, organic solvents, light stabilising agents, fluorescent brighteners.

15. A microbiocidal composition for combating pathogenic bacteria or fungi in veterinary medicine which comprise a bactericidally or fungicidally effective amount of at least one of the compounds of claim 1 and an inert carrier therefore.

16. A method of combating harmful bacteria or fungi which comprises applying an effective amount of at least one of the compounds of claim 1 to the bacteria or fungi or to the surface of a material to be protected therefrom.

17. A method of combating pathogenic bacteria of fungi in veterinary medicine which comprises using an effective amount of at least one of the compounds of claim 1.